KALANCHOE PLANT
Filed Sept. 25, 1974
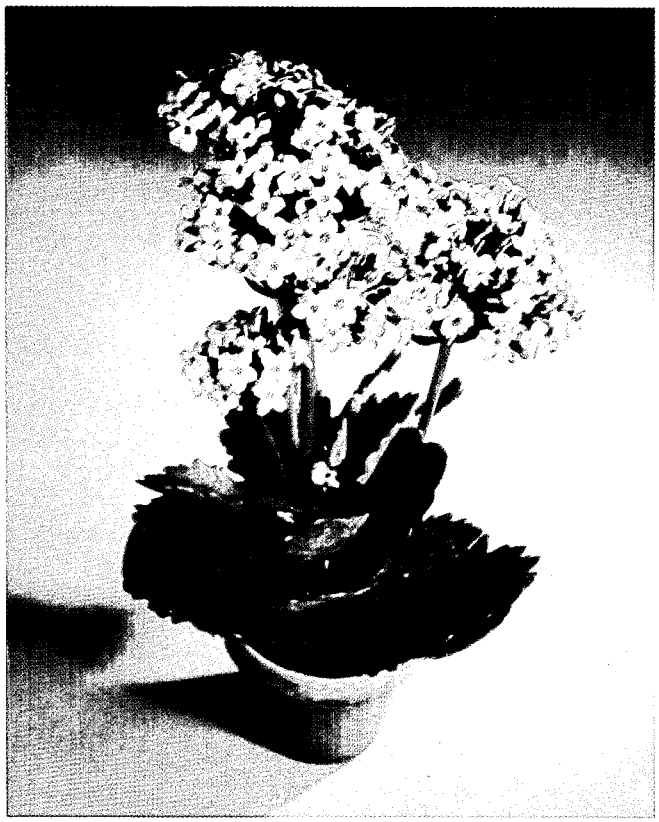

United States Patent

Plant Pat. 3,853
Patented Mar. 30, 1976

3,853

KALANCHOE PLANT

Adolf Grob, St Gallen, Switzerland, assignor to Mikkelsens Inc., Ashtabula, Ohio Filed Sept. 25, 1974, Ser. No. 509,143
Int. Cl. A01h 5/00
U.S. Cl. Plt.—68 1 Claim The present invention relates to a new and distinct variety of Kalanchoe plant known by the varietal name Feuerzauber.

The new variety was discovered by me as a selected, cultivated seedling derived from Grobs Rotglut, the unpatented seed parent, and Grobs Exotica, the unpatented pollen parent. The new cultivar was first asexually reproduced by vegetative cuttings at St. Gallen, Switzerland, and the unique characteristics of the new cultivar have been transmitted through successive propagations.

The new cultivar is particularly characterized by its very intense bright scarlet red colored flowers, strong roots, fast growing habit and relatively large flowers. The new cultivar is very reliable in commercial production, and is particularly suitable for flowering in April to November. The natural blooming season of the new cultivar is toward the end of February, although by steered culturing in the greenhouse, the cultivar can be brought to flowering during the entire year. Flowering response is 12–13 weeks in summer and 13–14 weeks in winter.

When compared to Feuerball, disclosed in my copending application Ser. No. 509,145, filed Sept. 25, 1974, perhaps the closest known cultivar, the new cultivar is uniquely characterized by its strong growth, its bright scarlet red flowers and by its larger flowers and foliage.

The following description is based on plants of the new cultivar grown initially in St. Gallen, Switzerland and subsequently in Ashtabula, Ohio. Flower color and foliage values are taken from RHS Colour Chart.

The accompanying color photographic drawing shows a typical blooming plant of the new cultivar, with the color being as true as possible with color illustrations of this type.

Parentage: The new cultivar is a seedling resulting from crossing the seed parent Grobs Rotglut, an unpatented Kalanchoe cultivar, with the pollen parent Grobs Exotica, also an unpatented Kalanchoe cultivar.

Propagation: By asexually propagating by vegetative cuttings, it has been successfully demonstrated that the new cultivar is stable and produces true to type.

Form: Bush form; numerous branches; upright and compact; very short but strong stems.

Growth habit: Upright and branching.

Rooting: The roots of the new cultivar are strong and above average in amount and texture when compared to other Kalanchoe varieties.

Blooming habit: Strong and rich flowering, reacts well to short day treatment.

Blooming season: Natural blooming season is toward the end of February, although by short day treatment, flowering of the cultivar is possible year around.

Foliage: Leaves are opposite, pinnately veined, above normal quantity showing no particular foliar abnormality, borne slightly above horizontal.

*Size.*—Average width approximately 6–8 cm. by 8–10 cm. in length, petiole 8 mm. to 10 mm. long.

*Shape.*—Elliptical, slight twisting.

*Texture.*—Smooth, thick, crisp, coriaceous.

*Margin.*—Strongly crenate.

*Color.*—Upperside, green 137A–B, very old leaves somewhat darker; lowerside, yellow 147–B.

Disease resistance: When grown with the cultivars Exotic Yellow and Exotic Gold infected with common powdery mildew, Feuerzauber does not become infected.

Flowers:

*Borne.*—On compound terminal paniculate cymes. Flower stems are strong and quite upright, forming a close flower cluster. Flowering stems are approximately 12 cm. to 14 cm. long, well balanced to the size of the base of the plant. Besides the apical flowering stem, considerable nodal flowering shoots occur giving a flowering appearance.

*Quantity.*—Flowering is quite profuse, uniform excepting later developing nodal shoots flowering after the initial apical shoot.

*Flower buds.*—Are more slender than those of Gelbe Melody or Solferinopurpur, disclosed respectively in my pending application Ser. Nos. 509,146 and 509,131, both filed Sept. 25, 1975, with the buds of Feuerzauber, measuring 3 mm. to 4 mm. before opening. Reverse of petals is pink, covered by four sepals.

*Petals.*—Four petals slightly overlapping, distinct midrib terminating in point on outer edge of petal; measuring 5 mm. wide by 8 mm. long, total flower diameter 15–16 mm. Color between Red 42A and 43A, reverse side near 41BC.

Reproductive organs:

*Stamens.*—Eight in number, anthers quite small compared to Gelbe Melody; uneven development, filaments light yellow green.

*Pollen.*—Light yellow pollen.

*Styles/ovaries.*—Light green styles, stigmas white crystalline appearance, four carpels developing multiple seed.

I claim:

1. A new and distinct cultivar of Kalanchoe characterized particularly by its bright scarlet red colored flowers; strong roots, fast growth habit, and by its abundant flowering and relatively large flowers.

No references cited.

ROBERT E. BAGWILL, Primary Examiner